United States Patent [19]

Ulrich et al.

[11] Patent Number: 5,247,841
[45] Date of Patent: Sep. 28, 1993

[54] APPARATUS FOR PRODUCING SAMPLE VAPOR FOR TRANSFERRAL INTO AN INDUCTIVELY COUPLED PLASMA

[75] Inventors: Andrea Ulrich, Hamburg; Stefan Meiners, Steinfurt; Rolf Tamm, Salem, all of Fed. Rep. of Germany

[73] Assignee: Bodenseewerk Perkin-Elmer GmbH, Uberlingen, Fed. Rep. of Germany

[21] Appl. No.: 823,509

[22] Filed: Jan. 21, 1992

[30] Foreign Application Priority Data

Jan. 24, 1991 [DE] Fed. Rep. of Germany ....... 4101956

[51] Int. Cl.⁵ .................... G01N 31/12; G01N 1/22
[52] U.S. Cl. ................ 73/864.81; 73/863.11; 73/23.41; 73/23.42
[58] Field of Search ............ 73/864.81, 863.11, 23.41, 73/23.42

[56] References Cited

U.S. PATENT DOCUMENTS

| | | | |
|---|---|---|---|
| 3,389,538 | 6/1968 | Carel | 55/386 |
| 3,901,672 | 8/1975 | Roberts | 73/864.81 |
| 3,940,994 | 3/1976 | Klee et al. | 73/864.81 |
| 4,100,806 | 7/1978 | Carbonnelle et al. | 73/863.11 |
| 4,191,541 | 3/1980 | Jenkins | 73/863.12 |
| 4,556,318 | 12/1985 | Barnes et al. | 356/36 |
| 4,594,904 | 6/1986 | Richter | 73/863.11 |
| 4,833,322 | 5/1989 | Forster et al. | 250/288 |
| 4,886,966 | 12/1989 | Matsunaga et al. | 313/362.1 |
| 4,955,717 | 9/1990 | Henderson | 250/288 |
| 4,974,453 | 12/1990 | Hohorst | 73/863.11 |
| 5,051,557 | 9/1991 | Satzger | 219/121.52 |

FOREIGN PATENT DOCUMENTS

| | | |
|---|---|---|
| 8122439 | 7/1984 | Fed. Rep. of Germany . |
| 8808551 | 10/1988 | Fed. Rep. of Germany . |
| 3735013 | 4/1989 | Fed. Rep. of Germany . |
| 3800189 | 7/1989 | Fed. Rep. of Germany . |
| 9003462 | 7/1990 | Fed. Rep. of Germany . |
| 3907454 | 9/1990 | Fed. Rep. of Germany . |
| 2033881 | 12/1970 | France . |
| 1398581 | 5/1990 | U.S.S.R. ............ 73/863.11 |
| 1431450 | 4/1976 | United Kingdom . |

*Primary Examiner*—Hezron E. Williams
*Assistant Examiner*—George Dombroske
*Attorney, Agent, or Firm*—Edwin T. Grimes

[57] ABSTRACT

A graphite tube for electrothermal vaporization of a sample to be investigated is held between annular contacts through which a flow can be passed lengthwise through the graphite tube. The contacts surround the graphite tube in a shell-like manner; a protective gas flow can thus be passed into a cavity which is formed between the graphite tube and the contacts. The contacts are retained in cooling blocks. The sample is introduced into the graphite tube, vaporized, and carried into the plasma by means of a carrier gas flow which is passed through the longitudinal bore of the graphite tube. The graphite tube contains a radial sample infeed opening which can be closed by a controllable closure member applied to the graphite tube.

6 Claims, 4 Drawing Sheets

APPARATUS FOR PRODUCING SAMPLE VAPOR FOR TRANSFERRAL INTO AN INDUCTIVELY COUPLED PLASMA

BACKGROUND OF THE INVENTION

The invention relates to an apparatus for producing sample vapor which is to be transferred into an inductively coupled plasma, containing (a) a graphite tube for the electrothermal vaporization of a sample to be investigated,
(b) annular contacts between which the graphite tube is held and through which a protective gas flow can be passed lengthwise through the graphite tube and which surround the graphite tube at a spacing to define an annulus therebetween through which a protective gas flow can be passed,
(c) cooling blocks in which the contacts are retained,
(d) sample supplying means for introducing a sample through a radial sample infeed opening into the graphite tube,
(e) closure means for closing the radial sample infeed opening of the graphite tube, and
(f) means for conveying the vaporized sample out of the closed graphite tube to the plasma by means of a carrier gas flow flowing through the longitudinal bore of the graphite tube.

"Plasma torches" using an inductively coupled plasma are known in the analytical technique. An inert gas is inductively excited such that a very hot plasma results. Samples are introduced into this plasma.

The plasma can then be used to excite the sample atoms to emit light. The spectral lines which are characteristic of certain looked-for elements are observed. The concentration of the looked-for elements in the sample can be inferred from the intensity of these spectral lines.

The plasma can also be used, however, to ionize the atoms of a sample and to pass the ionised atoms to a mass spectrometer. The plasma serves in this case as the ion source of the mass spectrometer.

It is known to spray sample liquid into the inductively coupled, hot plasma. During such operation, however, all constituents of the sample liquid including the solvent and possibly interfering components enter the plasma and perhaps the mass spectrometer.

Through the publication by Hall, Pelchat, Boomer and Powell entitled "Relative Merits of Two Methods of Sample Introduction in Inductively Coupled Plasma Mass Spectrometry: Electrothermal Vaporization and Direct Sample Insertion" in the "Journal of Analytical Atomic Spectrometry", Volume 3 (1988), pages 791 to 797, it is known to electrothermally vaporize a sample and convey the thus obtained sample vapor into the plasma by means of an argon carrier gas flow.

In the known arrangement the sample is deposited onto a platform which is held between two contacts or electrodes. The platform is heated to a high temperature by means of electric current passing through the contacts such as to vaporize the sample. The platform and the contacts are conjointly seated in a housing which is closed off by means of a cover made of quartz and shaped like a reverse funnel. The cover merges with a conduit leading to the plasma. Argon is passed into the housing and carries the vaporized sample into the plasma.

A publication by Wei-Lung Shen, Caruso, Fricke and Satzger entitled "Electrothermal Vaporisation Interface for Sample Introduction in Inductively Coupled Plasma Mass Spectrometry38 in the "Journal of Analytical Atomic Spectrometry", volume 5 (1990), pages 451 to 455, likewise describes an arrangement in which a sample is electrothermally vaporized and the sample vapor is passed into an inductively coupled plasma. The plasma serves as the ion source of a mass spectrometer.

In this known arrangement a graphite tub is held between two annular contacts. The contacts axially extend around the graphite tube. An annulus is thus formed between the contacts and the graphite tube. Through bores in the contacts, an outer protective gas flow is passed into the region of the two ends of the graphite tube. An "inner protective gas flow" likewise enters through a bore in one of the contacts in the region of a first end of the graphite tube into the longitudinal bore of the graphite tube. The contacts are retained in cooling blocks.

A conduit leading to the inductively coupled plasma extends from the cooling block in the region of the first end of the graphite tube. An axial conduit is inserted through a window at the opposite second end into the graphite tube. The conduit ends in a w-shaped loop which receives the sample and is placed at the center of the graphite tube. A carrier gas can also be introduced through this window into the longitudinal bore of the graphite tube by means of a carrier gas conduit. The graphite tube does not have a sample infeed opening in this construction.

The sample is supplied by inserting the w-shaped loop and electrothermally vaporized in the graphite tube. By means of a carrier gas flow, the vaporized sample is then conveyed from the second end of the graphite tube to the first end and via the conduit to the plasma.

An article by Crabi, Cavalli, Achilli, Rossi and Omenetto entitled "Use of the HGA 500 Graphite Furnace as a Sampling Unit for IPC Emission Spectroscopy" in "atomic spectroscopy", volume 3 (1982), pages 81 to 86, describes the use of a conventional graphite furnace for atomic absorption spectroscopy as vaporization apparatus for vaporizing a sample, whereby the sample vapor is carried along by a carrier gas into an inductively coupled plasma. The therein emitted characteristic spectral lines are observed.

In the known arrangement, the carrier gas flow is introduced through one of the inlets which are provided for the "inner" protective gas flow in the conventional use of such graphite furnaces. The remaining protective gas inlets are closed. A ring made of boron nitride extends between the cooling blocks in which the contacts are retained. The ring is held in a stainless steel housing. The stainless steel housing and the boron nitride ring have openings through which a sample can be infed into the graphite tube through the sample infeed opening thereof. One of the windows, through which the measuring light beam passes during atomic absorption spectroscopy, is removed and replaced by a connector for a conduit leading to the plasma.

In an apparatus for introducing samples into an inductively coupled plasma source mass spectrometer such as known, for example, from U.S. Pat. No. 4,886,966, a lengthwisely heated graphite tube has a radial sample infeed opening and is arranged between electrodes for electrothermal heating. One end of the graphite tube is connected to a protective gas source; the other end is connected to a plasma torch. The samples which are introduced into the graphite tube, are first dried and thereafter ashed or charred by electrothermal heating; during this stage the radial sample infeed opening remains in an open state for driving off the developed vapors or smoke. Thereafter, the radial sample infeed opening is closed by means of a plug and the graphite tube is electrothermally heated to atomization temperature. The inert gas flow is, then, used for conveying the atom vapor into the plasma torch and the mass spectrometer.

SUMMARY OF THE INVENTION

The invention is based on the object of enabling in an apparatus of the initially mentioned type, supply and treatment of a sample in a manner similar to that used in atomic absorption spectroscopy and rendering readily possible automation of the entire operation.

According to the invention, this object is achieved in that (g) said closure means contains a controllable closure member to be applied to the graphite tube for closing the radial sample infeed opening, and (h) the closure member is controlled by means of an actuating mechanism for movement between a first, retracted position, in which the closure member is laterally offset from the axis of the sample infeed opening, and a second, advanced position in which the closure member is applied to the graphite tube.

In this way, a sample pretreatment in the open state of the sample infeed opening can be effected in a manner similar to that used in conventional atomic absorption spectroscopy. Solvent vapors and smoke are carried away by the protective gas flows through the sample infeed opening. During subsequent vaporization of the actual sample, the sample infeed opening is closed by the closure member. A quantitative transfer of the sample vapors into the plasma by means of a carrier gas is thus ensured. The closure member is heated together with the graphite tube such that no carry-over of sample substance can occur due to the closure member.

BRIEF DESCRIPTION OF THE DRAWINGS

Exemplary embodiments of the invention are explained in greater detail hereinbelow with reference to the accompanying drawings.

DETAILED DESCRIPTION OF THE INVENTION

Figure 1:
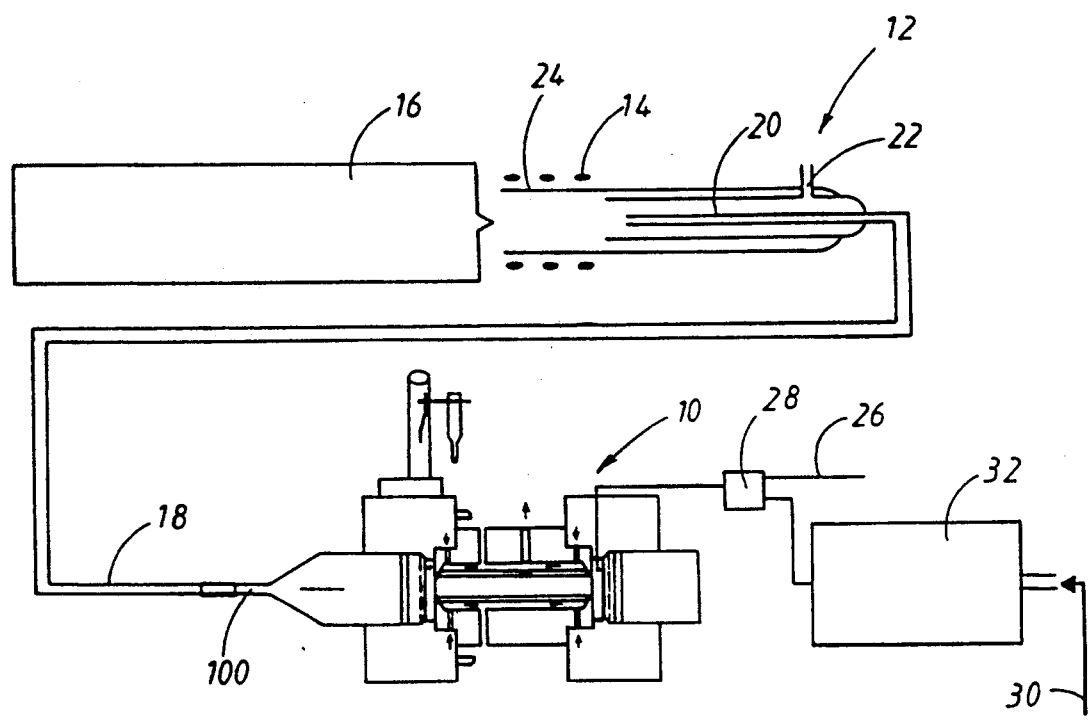
FIG. 1 is a schematic illustration and shows an apparatus for electrothermal vaporization of a sample in conjunction with a plasma torch and a mass spectrometer.

FIG. 1 shows the general structure of equipment having an apparatus 10 for electrothermal vaporization of the sample, a plasma torch 12 which produces an inductively coupled plasma by means of a coil 14, and a mass spectrometer 16 which is supplied with ionized plasma sample atoms from the plasma. The apparatus 10 is connected to the plasma torch 12 via a conduit 18. The conduit 18 is connected to a central tube 20 of the plasma torch 12, which tube ends upstream of the plasma region. An inert gas, e.g. argon, is supplied via a connector 22. The inert gas is inductively excited and forms the hot plasma in an area enclosed by a shell 24. The shell 24 is surrounded by the coil 14.

A protective gas flow is supplied to the apparatus 10 via a connector 26 and a valve 28 for protecting the graphite tube during the sample pretreatment, e.g. during the drying and ashing steps, and carries away vaporized solvent or smoke via the sample infeed opening. Alternatively, after pretreatment and during vaporization of the actual sample, a carrier gas can be switched onto the apparatus 10 by means of the valve 28. The carrier gas is supplied via a connector 30 and a flow controller 32.

Figure 2:
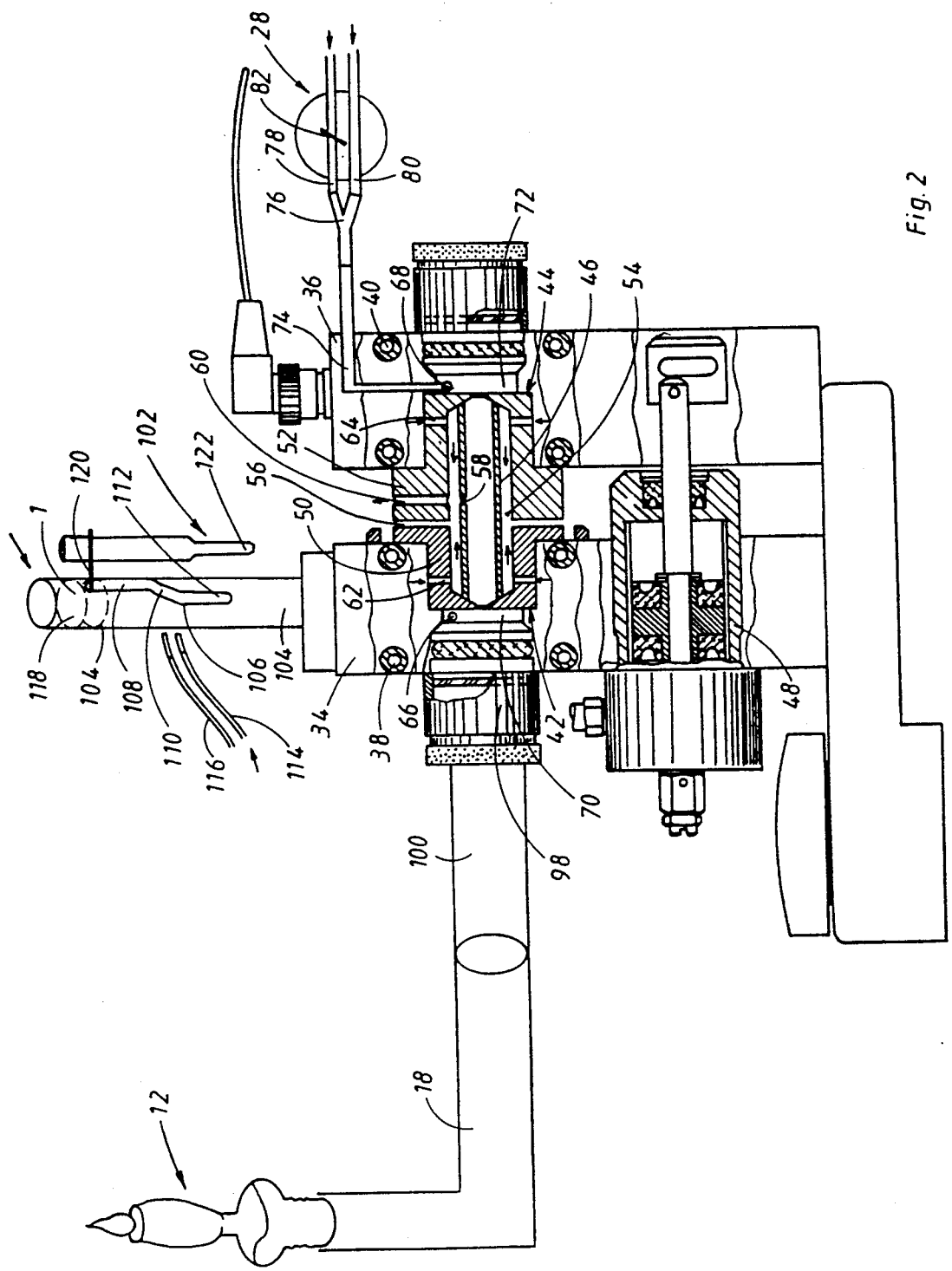
FIG. 2 shows a side view, partially in section, of a first embodiment of an apparatus for electrothermal vaporization of a sample and transfer of the sample vapor into an inductively coupled plasma.

The details of the apparatus 10 are depicted in FIG. 2.

The apparatus 10 is constructed in a manner similar to a conventional graphite furnace for electrothermal atomization of the sample used in atomic absorption spectroscopy. Such apparatus is illustrated and described, for example, in German Patent Nos. 24 13 782 or which are respectively cognate with U.S. Pat. Nos. 4,022,530 and 4,175,863. The apparatus 10 contains two cooling blocks 34 and 36 which are spaced from each other. The cooling blocks 34 and 36 are cooled by respective cooling coils 38 and 40 through which water is passed. Annular contacts 42 and 44, which are made of graphite, are seated in the cooling blocks 34 and 36, respectively. A graphite tube 46 acting as a graphite furnace is retained at its end faces between the contacts 42 and 44. The cooling blocks 34 and 36, along with the contacts 42 and 44, are biased at a constant contact force against the end faces of the graphite tube 46 by means of a pneumatic servomotor 48. The two cooling blocks 34 and 36 can be separated from each other by the servomotor 48 which enables the graphite tube 46 to be inserted or changed. The two contacts 42 and 44 contain respective annular sections 50 and 52 both of which surround the graphite tube 46 and extend from respective opposite ends thereof in the manner of a shell or jacket. An annulus 54 is formed between the sections 50 and 52 of the respective contacts 42, 44 and the graphite tube 46. The end faces of the sections 50 and 52 are arranged at a small distance from each other and define a gap 56 therebetween. The graphite tube 46 contains a radial sample infeed opening 58 in the center. A radial sample infeed opening 60 is provided in the section 52 of the contact 44 in alignment with the sample infeed opening 58 of the graphite tube 46. Furthermore, respective ducts 62 and 64 are bored in the contacts 42 and 44 in the region of the ends of the graphite tube 46 and through these ducts an "outer" protective gas flow can be introduced. The ducts 62 and 64 open into the annulus 54. The outer protective gas flow flows through the annulus 54 and thereby around the outer surface of the graphite tube 46. The outer protective gas flow, then, exits through the gap 56 and the sample infeed opening 60. When used in atomic absorption spectroscopy, this protective gas flow, then, flows off into the atmosphere. Furthermore, respective ducts 66 and 68 are formed in the cooling blocks. The ducts 66 and 68 open into respective axial bores 70 and 72 of the cooling blocks 34 and 36. The axial bores 70 and 72 are in alignment with the axial bores of the respective annular contacts 42 and 44 and the longitudinal bore of the graphite tube 46. Protective gas flows via the ducts 66 and 68 into the longitudinal bore of the graphite tube 46.

The above-described structure is that of a conventional graphite furnace as used in atomic absorption spectroscopy. Such graphite furnace is modified for the present application as follows:

The duct 68 leads to a conduit 74 which branches off to two branches 78 and 80 via a Y-member 76. The branch 80 is connected to the conventional protective gas connector 26 (FIG. 1). The branch 78 is connected to the carrier gas connector 30 via the flow controller 32. In the depicted exemplary embodiment, the valve arrangement 28 consists of a magnetically operated squeeze-type valve 82.

During conventional use of the graphite furnace such as in atomic absorption spectroscopy, a window is provided in a holder 98, as viewed on the left side of FIG. 1. This window is removed. A connector 100 made of ceramic material is inserted in its place. The conduit 18 leading to the plasma torch 12 is connected to the connector 100.

A closure apparatus 102 is provided for optionally closing the sample infeed opening 58 of the graphite tube 46. This closure apparatus contains a sleeve 104 which has a very flat structured S-shaped slot 106 extending lengthwise of the sleeve 104. The slot 106 has a straight section 108 extending lengthwise of the sleeve 104, a section 110 extending at an inclination to the longitudinal direction, and another straight section 112 connected thereto. A piston which can be subjected to compressed air on both sides, is guided within a pneumatic cylinder (not shown) which is arranged in the sleeve 104. The pneumatic cylinder may also be formed by a section of the sleeve 104. Compressed air can be applied to the pneumatic cylinder on either side of the piston via conduits 114 and 116. A guide member 118 is rotatably connected to the piston but axially held in position. A radial pin 120 is connected to the guide member 118. The pin 120 supports a closure member 122 which is made of graphite and extends in the lengthwise direction of the sleeve 104.

Figure 4:
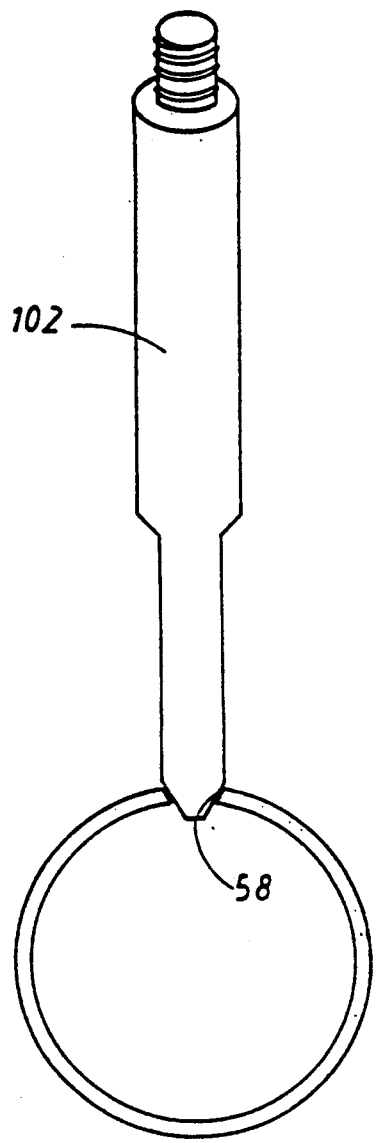
FIG. 4 shows at an enlarged scale, the engagement of a closure member with the sample infeed opening in an apparatus of the type as shown in FIG. 2 or 3.

By applying pressure to the piston on one or the other side, the closure member 122 can either be raised to the position depicted in FIG. 1 or placed into the sample infeed opening 58 of the graphite tube 46 through the sample infeed opening 60 of the shell section 52. In the latter case, the conical tip of the closure member 122 enters into the sample infeed opening 58. As evident from FIG. 4, the sample infeed opening 58 is of conical shape whereby the side walls of the sample infeed opening 58 define a cone having a cone angle of 30°. The conical tip of the closure member 122 likewise has a cone angle of 30°. The sample infeed opening 58 is thereby sealingly closed. In the raised position, the closure member 122 is displaced to the rear relative to the sample infeed opening 58. The sample infeed opening 58 thus is accessible, e.g. to a dosing tube of a conventional autosampler. The dosing of samples from the sample vessels of a turntable can thus be automated in a manner as already known in atomic absorption spectroscopy.

The arrangement described hereinbefore operates as follows:

The closure member 122 is at first in the raised position. The sample infeed opening is freely accessible. A sample liquid can be dosed into the graphite tube 46 using conventional means. This dosing operation can be automated in the manner as described in e.g. German Patent Number 26 02 675 which is cognate with U.S. Pat. No. 4,068,529.

The sample can be pretreated in a manner similar to that used in atomic absorption spectroscopy, i.e. dried and ashed. Solvent vapors and smoke are carried away by the inner protective gas flow through the sample infeed openings 58 and 60. The magnetically operated squeeze-type valve 82 is still closed at this time.

The closure member 122 is then lowered. The sample infeed opening 58 is closed by the closure member. The graphite tube 46 is heated to the atomizing or vaporizing temperature such that now the actual sample is vaporized. The squeeze-type valve 82 is simultaneously opened. A carrier gas flow enters through duct 68 into the bore of the graphite tube 46 and carries the vaporized sample to the plasma torch 12 via conduit 18. The plasma torch 12 operates as the ion source of the mass spectrometer 16. The atoms of the sample are ionized and detected by the mass spectrometer 16.

Figure 3:
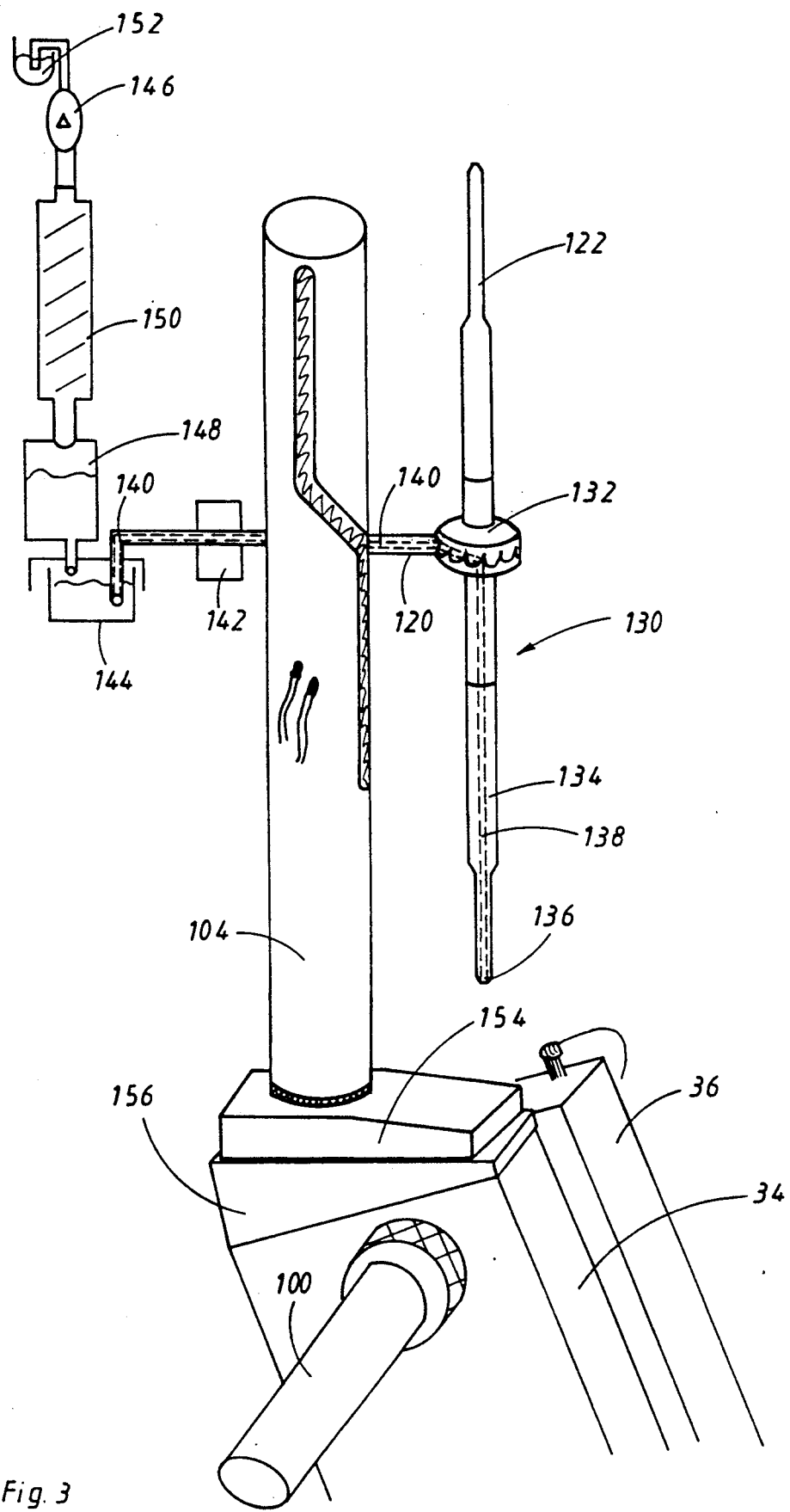
FIG. 3 is a schematic perspective illustration of a modified embodiment.

FIG. 3 shows a modified embodiment which largely corresponds to the embodiment shown in FIG. 2, particularly also with respect to the basic structure of the graphite furnace which is not shown in detail in FIG. 3. The arrangement shown in FIG. 3 is set up for sucking off the solvent vapors and smoke from the graphite tube during the sample pretreatment.

The closure apparatus 130 contains a support 132 which is attached to the pin 120 so that it can be rotated by 180° about the axis of the pin 120. A closure member 122 corresponding to the closure member shown in FIG. 2 is arranged on one side of the support 132. A suction tube 134 is provided at the support 132 and offset by 180° relative to the closure member 122. The suction tube 134 likewise is made of graphite. The suction tube 134 contains a conical tip 136 similar to the tip of the closure member 122. A longitudinal duct 138 is formed in the suction tube 134. The longitudinal duct 138 opens into the tip 136. The longitudinal duct 138 is in communication with a duct 140 in the pin 120.

As schematically illustrated in FIG. 3, the pin 120 can be pivoted by 180° between a (depicted) first and a second position by means of a swivel motor 142. During this operation, the support 132 is also rotated by 180° about the axis of the pin 120. In the first position, the suction tube 134 points downwards. In the second position, the closure member 122 points downwards. The duct 140 is led to a rinse or waste vessel 144 which can be filled with water. Some of the sucked-off components are dissolved therein. The vapor above the surface of the liquid in the rinse or waste vessel is sucked through a filter 148 and an adsorption column 150 by means of a pump 146. The outlet side of the pump 146 is connected to the atmosphere via a further, water-filled wash vessel 152.

In this manner, the vapors formed during the sample pretreatment do not enter directly into the atmosphere. The user is protected against such vapors.

Figure 5:
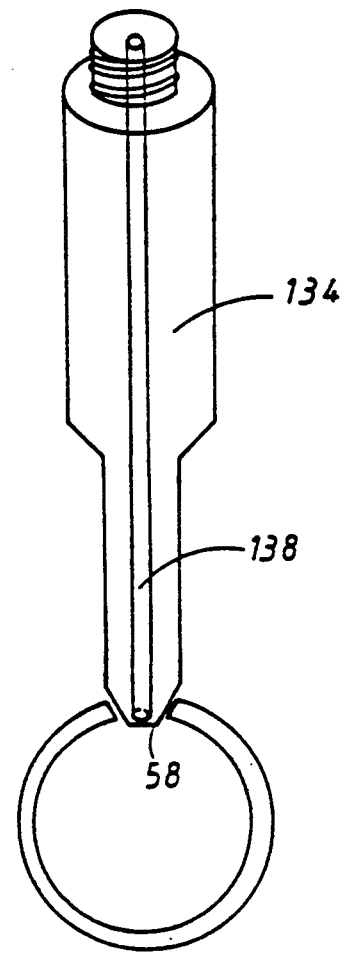
FIG. 5 shows, at an enlarged scale, the engagement of a suction tube with the sample infeed opening in an apparatus of the type as shown in FIG. 3.

When the sample is pretreated by drying and ashing, the support 132 is turned into the depicted first position by the swivel motor 142. The support 132 with the suction tube 134 pointing downwards is then introduced through the sample infeed opening 60 and inserted into the sample infeed opening 58 of the graphite tube 46. The tip 136 of the suction tube thus enters the conical sample infeed opening 58. This is shown in FIG. 5 at an enlarged scale. When the sample is dried and ashed, the formed vapors and the like are sucked away via the suction tube. The drying time can also be reduced thereby.

Thereafter, the suction tube is withdrawn from the graphite tube 46 and the sample infeed opening 60. The support 132 is rotated by 180° such that the closure member 122, then, points downwards. The support 132 is moved downwards. The closure member 122 is placed into the sample infeed opening 58 of the graphite tube 46 and closes off this sample infeed opening 58. The sample is then vaporized in the described manner and the vapor is carried to the plasma by the carrier gas flow.

As can be seen best in FIG. 3, the axis of the sleeve 104 is inclined by an angle of 27° relative to a line extending normally to the top side of the cooling block 34. To this end, the sleeve 104 is supported by means of a base 154 and a wedge member 156 at this top side. The direction of movement of the closure member 122 or the suction tube 134, as the case may be, is correspondingly inclined. This inclination takes into consideration the fact that the sample infeed openings 58 and 60 are also offset by this angle relative to the vertical. Such inclination of the sample infeed opening 58, to which the sample infeed opening 60 in the section 52 of the contact 44 is aligned, is preferable for platform atomization as known from U.S. Pat. No. 4,303,339.

During the sample vaporization, there is not only heated the graphite tube 46 but also the closure member 122. The separation of the closure member and the graphite tube advantageously occurs only after the graphite tube has cooled off again subsequent to the vaporizing and heating operations.

What is claimed is:

1. Apparatus for producing sample vapor which is to be transferred into an inductively coupled plasma, comprising:
   (a) a graphite tube for electrothermal vaporization of a sample to be investigated,
   (b) annular contacts between which the graphite tube is held and through which a protective gas flow can be passed lengthwise through the graphite tube and which surround the graphite tube at a spacing to define an annulus therebetween through which a protective gas flow can be passed,
   (c) cooling blocks in which the contacts are retained,
   (d) sample supplying means for introducing a sample through a radial sample infeed opening into the graphite tube,
   (e) closure means for closing the radial sample infeed opening of the graphite tube,
   (f) said closure means containing a controllable closure member to be applied to the graphite tube for closing the radial sample infeed opening,
   (g) an actuating mechanism for controlling movement of said controllable closure member between a first, retracted position, in which the closure member is laterally offset from the axis of the sample infeed opening, and a second, advanced position in which the closure member is applied to the graphite tube,
   (h) means for conveying the vaporized sample out of the closed graphite tube to the plasma by means of a carrier gas flow flowing through a longitudinal bore of the graphite tube, and
   said closure member being seated at a support guided in a sleeve, said support being movable along the sleeve by means of a servomotor seated in the sleeve, and being guided in a guideway provided in the sleeve by means of a pin.

2. Apparatus according to claim 1, further including a suction tube to be applied to the sample infeed opening of the graphite tube by means of said actuating mechanism.

3. Apparatus according to claim 2, further including:
   (a) a support supporting the closure member and the suction tube in coaxial relationship at an angular offset of 180° relative to each other; and
   (b) a swivel motor drivingly connected to said support for selectively pivoting either said closure member or said suction tube into operating position.

4. Apparatus for producing sample vapor for transferal into an inductively coupled plasma, comprising:
   a graphite tube for electrothermal vaporization of a sample to be investigated;
   annular contacts for holding the graphite tube and passing an electric current therethrough;
   said annular contacts contacting said graphite tube at respective opposite ends thereof and extending around said graphite tube from said opposite ends at a spacing therefrom such as to define an annulus between said annular contacts and said graphite tube;
   said annular contacts containing respective passage means for passing a flow of protective gas lengthwise through said graphite tube and through said annulus;
   cooling blocks retaining respective ones of said annular contacts;
   said graphite tube containing a radial sample infeed opening;
   closure means containing a closure member for closing said radial sample infeed opening of said graphite tube;
   said closure member being mounted at a support member;
   reciprocating means for reciprocating said closure member between a retracted inoperative position distant from said graphite tube and an advanced operative position in which said closure member closes said radial sample infeed opening.
   said reciprocating means containing a guide sleeve for guiding said support member of said closure member during reciprocation thereof;
   said guide sleeve containing a guideway receiving said support member for said reciprocation of said closure member, said guideway defining a first section, in which said closure member is aligned with said radial sample infeed opening, and a second section which is connected with said first section and in which said closure member is out of alignment with said radial sample infeed opening;
   said guide sleeve accommodating a servomotor acting on said support member for reciprocating said closure member between said inoperative and operative positions; and
   means for conveying vaporized sample, in the operative position of said closure member, from the graphite tube to the plasma by means of a carrier gas flow through a longitudinal bore of said graphite tube.

5. The apparatus according to claim 4, further including a suction tube for insertion into the radial sample infeed opening of the graphite tube.

6. The apparatus according to claim 5, further including:
(a) a support supporting the closure member and the suction tube in coaxial relationship at an angular offset of 180° relative to each other; and
(b) a swivel motor drivingly connected to said support for selectively pivoting either said closure member or said suction tube into an operating position.

* * * * *